US008895243B2

(12) United States Patent
Maekawa et al.

(10) Patent No.: US 8,895,243 B2
(45) Date of Patent: Nov. 25, 2014

(54) METHOD OF ASSESSING CANCEROUS CONDITIONS AND REAGENT FOR DETECTING GENE PRODUCT TO BE USED IN THE METHOD

(71) Applicant: Sekisui Medical Co., Ltd., Tokyo (JP)

(72) Inventors: Masato Maekawa, Hamamatsu (JP); Takeshi Uramoto, Ryugasaki (JP)

(73) Assignee: Sekisui Medical Co., Ltd., Tokyo (JP)

( * ) Notice: Subject to any disclaimer, the term of this patent is extended or adjusted under 35 U.S.C. 154(b) by 0 days.

(21) Appl. No.: 13/686,128

(22) Filed: Nov. 27, 2012

(65) Prior Publication Data

US 2013/0172200 A1 Jul. 4, 2013

Related U.S. Application Data

(62) Division of application No. 11/722,007, filed as application No. PCT/JP2005/023020 on Dec. 15, 2005, now abandoned.

(30) Foreign Application Priority Data

Dec. 17, 2004 (JP) ................. 2004-366206

(51) Int. Cl.
*C12Q 1/68* (2006.01)
*C07H 21/02* (2006.01)
*C07H 21/04* (2006.01)
*G01N 33/574* (2006.01)

(52) U.S. Cl.
CPC ............ *C12Q 1/6886* (2013.01); *G01N 33/574* (2013.01)
USPC .......................... 435/6.1; 536/23.1; 536/24.3

(58) Field of Classification Search
CPC ........... C12Q 1/6886; C12Q 2535/131; C12Q 2545/114
See application file for complete search history.

(56) References Cited

U.S. PATENT DOCUMENTS

| | | | |
|---|---|---|---|
| 5,541,308 | A | 7/1996 | Hogan et al. |
| 6,582,908 | B2 | 6/2003 | Fodor et al. |
| 6,773,882 | B2 | 8/2004 | Hogan et al. |
| 6,812,339 | B1 | 11/2004 | Venter et al. |
| 7,214,786 | B2 | 5/2007 | Kovalic et al. |
| 7,557,201 | B2 | 7/2009 | Fincher et al. |
| 7,745,391 | B2 | 6/2010 | Mintz et al. |
| 2003/0186309 | A1 | 10/2003 | Scott et al. |

FOREIGN PATENT DOCUMENTS

| | | |
|---|---|---|
| JP | 2003 135073 | 5/2003 |
| JP | 2003 164288 | 6/2003 |
| WO | 01/66719 | 9/2001 |

OTHER PUBLICATIONS

Michiels et al. Lancet, 2005; 365:488-492.*
Slonin, Nature Genetics Supplement, vol. 32, Dec. 2002, pp. 502-508.*
Cheung et al (Nature Genetics, vol. 33, pp. 422-425; (2003).*
Nagao et al; Human molecular Genetics, vol. 14, pp. 3379-3388, 2005.*
Fujii, et al., Mutations in the Human Homologue of Drosophila patched in Japanese Nevoid Basal Cell Carcinoma Syndrome Patients, Human Mutation,vol. 21, No. 4, pp. 451-452, 2003.
Lam, et al., "Novel mutations in the Patched gene in basal cell nevus syndrome", Molecular Genetics and Metabolism, vol. 76, No. 1, pp. 57 -61, 2002.
Dong, at al., "Identification of Patched Mutations in Medulloblastomas by Direct Sequencing", Human Mutation, vol. 16, No. 1, pp. 89-90, 2000.
Savino, at al.,"Spectrum of PTCH Mutations in Italian Nevoid Basal Cell-Carcinoma Syndrome Patients: Identification of Thirteen Novel Alleles". Human Mutation, vol. 24, No. 5, pp. 441, 2004.
Smyth, et al., "The effects of splice site mutations in patients with naevoid basal cell carcinoma syndrome", Human Genet, vol. 102, No. 5, pp. 598-601, 1998.
Vorechovsky, et al., "Somatic mutations in the human homologue of Drosophila patched in primitive neuroectodermal tumours", Oncogene. vol. 15, No. 3, pp. 361-366, 1997.
Shevchenko, et al., "Mutation Screening Using Automated Bidirectional Dideoxy Fingerprinting", Biotechniques, vol. 28, No. 1, pp. 134-138, 2000.
Maekawa, et al., "Taieki Shindan eno oyo o Mezashita Shuyo no biomarker no Kaihatsu ni Kansuru Kenkyu", Kosei Rodo Kagaku Kenkyuhi Hojokin Dai 3ji Tai Gan Sogo Senryaku Kenkyu Jigyo Gan Kenshin ni yuyo na Atarashii Shuyo Marker no Kaihtsu Sokatsu Buntan Kenkyu Hokokusho, pp. 10-15, 2005. (with partial English translation).
Pastorino, at al.,"Molecular Characterization of Italian Nevoid Basal Cell Carcinoma Syndrome Patients", Human Mutation, vol. 25, No. 3, pp. 322-323, 2005.
Nagao, at al., "Detecting tissue-specific alternative splicing and disease-associated aberrant splicing of the PTCH gene with exon junction microarrays", Human Mol Genet, vol. 14, No. 22, pp. 3379-3388, 2005.
Kappler, et al., "Profiling the molecular difference between Patched- and p53-dependent rhabdomyosarcoma", Oncogene, vol. 23, No. 54, pp. 875-8795, 2004.
Chang-Claude, et al., "The Patched Polymorphism Pro1315leu (C3944T) may modulate the Association between use of Oral Contraceptives and Breast Cancer Risk", International Journal of Cancer, vol. 103, No. 6, pp. 779-783, 2003.
NEB catalog (1998/1999 pp. 121, 284).
Kogerman, et al., Oncogene 2002, vol. 21, p. 6007.

(Continued)

*Primary Examiner* — Jehanne Sitton
(74) *Attorney, Agent, or Firm* — Oblon, Spivak, McClelland, Maier & Neustadt, L.L.P.

(57) ABSTRACT

A reagent for detecting gene product, the reagent comprising a probe or chemical modulation that specifically binds to an alternative splicing junction of a gene product of human PTCH1 gene, the expression of the gene product from gene products of the human PTCH1 gene being varied due to the unusual alternative splicing, for use for measuring the abundance of the gene product contained in a human sample.

6 Claims, 7 Drawing Sheets

(56) References Cited

OTHER PUBLICATIONS

Office Action issued Aug. 9, 2011 in Japanese Patent Application No. 2006-548894 (w/English translation).

Kazuaki Nagao, et al., "Identification and Characterization of human and mouse Patched isoforms generated by alternative splicing". The Annual Meeting of the Molecular Biology Society of Japan. Program and Lecture Abstract, W3E-3, vol. $27^{th}$, p. 376, Nov. 25, 2004, 4 pages (w/English Translation).

* cited by examiner

METHOD OF ASSESSING CANCEROUS CONDITIONS AND REAGENT FOR DETECTING GENE PRODUCT TO BE USED IN THE METHOD

TECHNICAL FIELD

The present invention relates to a method of assessing cancerous conditions of samples derived from humans and a reagent for detecting gene product to be used in the method.

BACKGROUND ART

Genome analysis provides an estimation that the total gene number in human genome is about 22,000 and an anticipation that the alternative splicing mechanism is carried out in 50 to 60% of the number of genes. Alternative splicing mechanism is a reasonable and efficient gene expression regulation mechanism, which involves a plurality of ways of removing introns upon a splicing where an intron region is cleaved from an RNA precursor, a gene product, and two exons upstream and downstream linked each other, so that a single gene can produce a plurality of proteins having different localization and properties. With respect to how the information of presumably 100,000 or more proteins is coded in 22,000 genes and expressed in a human body, the alternative splicing is considered to make up the gap in number.

On the other hand, it has been shown that canceration of cells be caused by gene mutation or abnormal gene expression regulation. Abnormal occurrence of splice variants due to abnormal regulation of alternative splicing in intracellular gene products such as transcription products and translation products thereof may be one of factors of canceration of cells.

For example, human cell adhesion molecule (hyaluronic acid receptor), CD44, has 20 types of identified splice variant transcription products and it has been elucidated that the expression ratios of splice variant transcription products significantly differ: at least between cancerous pleural effusion and non-cancerous pleural effusion; and between urine from a patient with bladder cancer and urine from a patient without cancer. The expression ratios of the splice variant transcription products are also applied to clinical tests as a method of distinguishing cancerous cells from normal cells.

Canceration of cells is a phenomenon caused by abnormal expression of a plurality of genes and the mechanism thereof remains to be elucidated. It is known that mutations of genes and expression abnormalities that are involved in canceration of cells are varied depending on tissues from which cancerous cells are derived and degree of canceration of cells.

Therefore, besides the above-mentioned CD44, new cancer markers for use in cancer diagnosis well matched for various cancers are required, which can also be utilized as the targets in drug discovery. In particular, there are expectations, properly and accurately understanding the conditions of cancer cells causing cancer diseases, that cancer markers be provided useful for obtaining the correlation between different conditions of cancer cell and cancer disease.

Regarding cancer markers, the Patent Document 1 described below discloses novel ATPase-like polypeptide and its DNA expressed in a human monocyte cell line THP-1. The polypeptide is a 10-transmembrane protein having three P-type ATPase regions in the cell membrane and is a novel ATPase-like polypeptide having a 1192 amino acid sequence or a deleted mutant (splice variant) having a 1129 amino acid sequence in which 63 amino acids in the cell membrane is deleted. The polypeptide is confirmed to express with increased ratios in cancer cells, in particular gastric cancer cells, so that the polypeptide is useful as a novel cancer marker.

Regarding application of splice variants to pharmaceuticals and diagnosis of disease, Patent Document 2 discloses an identification of novel splice variant of MAP kinase p38α resulting from alternative splicing, cloning a gene coding the variant and an elucidation of the structure and function of the gene.

On the other hand, PTCH1 gene, which is one of Hedgehog signal genes, is known to play an important role in the developmental process of multicellular organisms and in the maintenance of functions of adults. In humans, PTCH1 gene is known to be a causative gene for genetic diseases accompanied by congenital malformation such as basal cell nevus syndrome. PTCH1 gene is also reported to be involved in basalioma, medulloblastoma, etc. as a cancer suppressor gene (see Patent Documents 1 and 2 below).
Patent Document 1: JP 2003-164288 A
Patent Document 2: JP 2003-135073 A
Non Patent Document 1: Kappler R. et al. Oncogene. 2004 Nov. 18; 23(54): p 8785-95
Non Patent Document 2: Chang-Claude J. et al. Int. J. Cancer 2003 Mar. 1; 103(6): p 779-83

DISCLOSURE OF INVENTION

Problems to be Solved by the Invention

It is an object of the present invention to provide a novel cancer marker useful for the diagnosis of cancers in therapy or preventive therapy or maintenance therapy treatment of cancer diseases, and a method of determining a cancerous conditions using the cancer marker.

Means for Solving the Problems

To achieve the above-mentioned object, the inventors of the present invention made an extensive search on splice variant transcription products, which are gene products of PTCH1, one of Hedgehog signaling genes and as a result they have discovered four novel splice variant transcription products, accomplishing the present invention.

That is, a method of determining cancerous conditions of the present invention is a method of determining cancerous conditions of a human-derived sample, and includes determining cancerous conditions of the human-derived sample by using an abundance of a gene product of human PTCH1 gene contained in the sample as an index, the expression of the gene product from gene products of said human PTCH1 gene being varied due to the unusual alternative splicing.

According to the method of determining a cancerous conditions of the present invention, the cancerous conditions of the sample can be determined using as an index the abundance of a gene product from gene products derived from human PTCH1 gene, the expression of the gene product being varied due to the unusual alternative splicing.

Further, another method of determining cancerous conditions of the present invention is a method of determining cancerous conditions of a human-derived sample, and includes the steps of: (1) measuring an abundance of at least one transcription product from transcription products of human PTCH1 gene contained in the human-derived sample, in which the transcription product of which the abundance is measured contains, in an RNA sequence thereof, at least one base sequence selected from the group consisting of (a) base sequences described in SEQ ID Nos. 1 to 4, and (b) base sequences having deletion, substitution, and/or insertion of one to several bases in the base sequences described in SEQ ID Nos. 1 to 4 and having ability to hybridize respectively with corresponding complementary strands of the base sequences described in SEQ ID Nos. 1 to 4 under stringent conditions; and (2) determining cancerous conditions of the human-derived sample by using the measured abundance of the transcription product in the human-derived sample as an index.

In this case, it is preferable that the method of determining cancerous conditions, further include the step of measuring an abundance of at least one transcription product from transcription products of human PTCH1 gene contained in a control sample which is obtained from a normal human living body tissue, in which the transcription product of which the abundance in the control sample is measured contains, in an RNA sequence thereof, at least one base sequence selected from the group consisting of (a) base sequences described in SEQ ID Nos. 1 to 4, and (b) base sequences having deletion, substitution, and/or insertion of one to several bases in the base sequences described in SEQ ID Nos. 1 to 4 and having ability to hybridize respectively with corresponding complementary strands of the base sequences described in SEQ ID Nos. 1 to 4 under stringent conditions, and in which the step of determining cancerous conditions of the human-derived sample is performed by comparing the measured abundance of transcription product in the human-derived sample with the measured abundance of the transcription product in the control sample.

According to the above-mentioned mode of the present invention, the cancerous conditions of the sample can be determined using as an index the abundance of a transcription product from transcription products derived from human PTCH1 gene, the expression of the transcription product being varied due to the unusual alternative splicing. Further, comparison with the abundance of the transcription product in control sample collected from a human normal living tissue enables more accurate determination of cancerous conditions of the sample.

In the method of determining cancerous conditions of the present invention, it is preferable that the abundance of the transcription product is measured by a method in which the transcription product is detected by using a probe or chemical modulation thereof that binds sequence-specifically to the complementary strand of at least one base sequence selected from the group consisting of (a) bases sequences described in SEQ ID Nos. 1 to 4, and (b) base sequences having deletion, substitution, and/or insertion of one to several bases in the base sequences described in SEQ ID Nos. 1 to 4 and having ability to hybridize respectively with corresponding complementary strands of the base sequences described in SEQ ID Nos. 1 to 4 under stringent conditions.

In this case, the probe or chemical modulation thereof may include a polynucleotide, a polyribonucleotide, chemical modulations thereof, and a polynucleotide, polyribonucleotide or chemical modulations thereof having a base sequence selected from those sequences having substitution, insertion, and/or deletion of one or more bases such that sequence-specific binding ability to the complementary strand of nucleic acid is not impaired.

According to the above-mentioned mode of the present invention, presence of a transcription product whose expression varies due to the unusual alternative splicing can be detected simply and specifically with high sensitivity.

Further, another method of determining cancerous conditions of the present invention is a method of determining cancerous conditions of a human-derived sample, and includes the steps of: (1) measuring an abundance of a translation product from at least one transcription product from transcription products of human PTCH1 gene contained in the human-derived sample, in which the transcription product from which the abundance of the translation product is measured contains, in an RNA sequence thereof, at least one base sequence selected from the group consisting of (a) base sequences described in SEQ ID Nos. 1 to 4, and (b) base sequences having deletion, substitution, and/or insertion of one to several bases in the base sequences described in SEQ ID Nos. 1 to 4 and having ability to hybridize respectively with corresponding complementary strands of the base sequences described in SEQ ID Nos. 1 to 4 under stringent conditions; and (2) determining cancerous conditions of the human-derived sample by using the measured abundance of the translation product in the human-derived sample as an index.

In this case, it is preferable that the method of determining cancerous conditions, further include the step of measuring an abundance of a translation product from at least one transcription product from transcription products of human PTCH1 gene contained in a control sample which is obtained from a normal human living body tissue, in which the transcription product from which the abundance of the translation product in the control sample measured contains, in an RNA sequence thereof, at least one base sequence selected from the group consisting of (a) base sequences described in SEQ ID Nos. 1 to 4, and (b) base sequences having deletion, substitution, and/or insertion of one to several bases in the base sequences described in SEQ ID Nos. 1 to 4 and having ability to hybridize respectively with corresponding complementary strands of the base sequences described in SEQ ID Nos. 1 to 4 under stringent conditions, and in which the step of determining cancerous conditions of the human-derived sample is performed by comparing the measured abundance of the translation product in the human-derived sample with the measured abundance of the translation product in the control sample.

According to the above-mentioned mode of the present invention, the cancerous conditions of the sample can be determined using as an index the abundance of a translation product from translation products from transcription products derived from human PTCH1 gene, the expression of the translation product being varied due to the unusual alternative splicing. Further, comparison with the abundance of the translation product in control sample collected from a normal human living tissue enables more accurate determination of cancerous conditions of the sample.

In the method of determining cancerous conditions of the present invention, it is preferable the human-derived sample and the control sample obtained from the normal human living body tissue be samples obtained from the same subject.

In the method of determining cancerous conditions of the present invention, the human-derived sample is preferably a specimen obtained from human. In this case, the human-derived sample may be a human living body tissue.

Further, in the method of determining cancerous conditions of the present invention, it is preferable that the human-derived sample be a sample extracted from at least one organ selected from the group consisting of colon, leukocyte, brain, and lung.

In the method of determining cancerous conditions of the present invention, the abundance of the transcription product can be measured preferably by a micro-array method, an RT-PCR method, a real time PCR method, a subtraction method, a differential display method, a differential hybridization method, or a cross hybridization method, and the abundance of the translation product form the transcription product can be measured preferably by a Western blotting method or an ELISA method.

On the other hand, a reagent for detecting gene product of the present invention is a reagent for detecting gene product, and the reagent includes a probe or chemical modulation that specifically binds to a gene product of human PTCH1 gene, the expression of the gene product from gene products of the human PTCH1 gene being varied due to the unusual alternative splicing, so that the reagent can be use for measuring the abundance of the gene product contained in a human-derived sample.

In this case, the gene product is a transcription product of human PTCH1 gene contained in the human-derived sample and it is preferable that the probe or chemical modulation thereof is a probe or chemical modulation that sequence-specifically binds to the complementary strand of nucleic acid of the transcription product whose expression is varied.

Further, in case that the gene product is a translation product from a transcription product of human PTCH1 gene contained in the human-derived sample, the probe or chemical modulation thereof can be an antibody or chemical modulation thereof that specifically binds to the translation product whose expression is varied.

With the reagent for detecting gene product of the present invention, the presence of gene product, transcription product or translation product, whose expression is varied due to the unusual alternative splicing, among from gene products derived from human PTCH1 gene can be detected simply and specifically with high sensitivity.

In the reagent for detecting gene product of the present invention, the probe or chemical modulation thereof may include a probe or chemical modulation thereof that binds sequence-specifically to base sequence selected from the group consisting of (a) base sequences described in SEQ ID Nos. 1 to 4, and (b) base sequences having deletion, substitution, and/or insertion of one to several bases in the base sequences described in SEQ ID Nos. 1 to 4 and having ability to hybridize respectively with corresponding complementary strands of the base sequences described in SEQ ID Nos. 1 to 4 under stringent conditions.

In this case, it is preferable that the probe or chemical modulation thereof includes a polynucleotide, a polyribonucleotide, chemical modulations thereof, and a polynucleotide, polyribonucleotide or chemical modulations thereof having a base sequence selected from those sequences having substitution, insertion, and/or deletion of one or more bases such that sequence-specific binding ability to the complementary strand of nucleic acid is not impaired.

In these modes of the reagent for detecting gene products of the present invention, it is easy to prepare probes or chemical modulations thereof for detecting the gene products specifically with high sensitivity.

When the chemical probes or chemical modulations thereof include 15 to 30 base-long oligonucleotides, many samples can be processed speedily by utilizing conventional RNA quantitation technology, which is suitable for quantitation of trace amount of RNA.

Effects of the Invention

According to the present invention, using a gene product whose expression is varied due to the unusualness of alternative splicing from the gene products derived from human PTCH1 gene as a cancer marker, it is allowed to provide a simple and specific method of determining a cancerous conditions of a human-derived sample and to provide a reagent for detecting gene product for use in such a method.

BEST MODE FOR CARRYING OUT THE INVENTION

Figure 1:
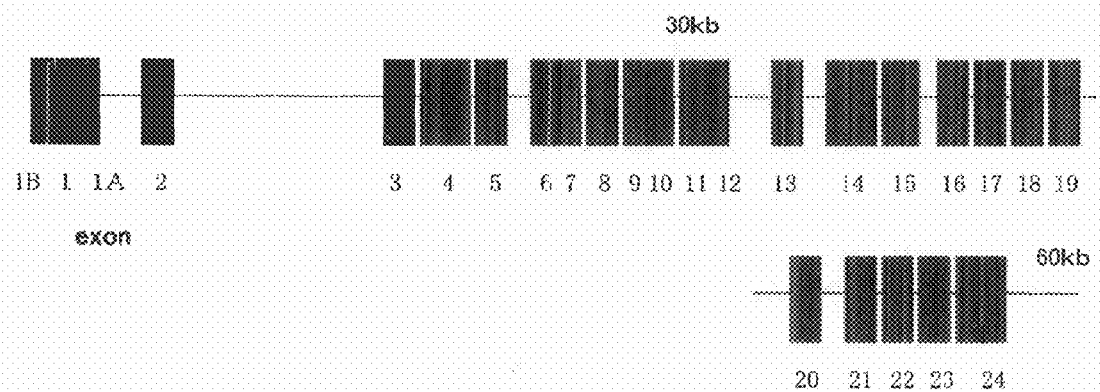
FIG. 1 A schematic diagram illustrating a gene structure of human PTCH1 gene that is used as a marker gene in the present invention.

In the present invention, "cancerous conditions" has a meaning generally understood in the art and specifically means a degree of malignance as a cancer when the sample consists of cells, or a degree of metastasis when the sample is, for example, a cancer cell of a metastatic nature, or abundance ratio or the like of cancer cells in a cell assembly when the sample is an assembly of cells.

In the present invention, "human-derived sample" is not particularly limited and includes liquid living body samples such as blood, serum, plasma, spinal fluid, urine, and sperm; organ tissue fragment samples such as heart, brain, pancreas, lung, liver, bone, kidney, bladder, spleen, thyroid gland, testis, uterus, small intestine, and colon; samples prepared therefrom by various methods so that they can be easily assayed, for example, for gene products, transcription products, and translation products thereof. Such a pretreatment includes, for example, RNA extraction and protein purification and so on, which can be performed by known methods.

In the present invention, "control sample which is obtained from normal human living body tissue" is not particularly limited as far as the sample can be used as a standard for determining cancerous conditions. For example, a tissue fragment, which is obtained from a human living tissue, and cells of which are determined normal by a cell test according to a known determination method, can be used as a control sample.

In the present invention, "transcription product" has a meaning generally understood in the art and specifically refers to, for example, RNA synthesized by RNA polymerase that transcribes genes on the genome in a cell, mRNA precursor, mature mRNA, and modulations thereof.

In the present invention, "translation product" has a meaning generally understood in the art and specifically refers to, for example, polypeptide precursor and polypeptide synthesized by ribosome that translate mRNA as the above-mentioned transcription product, and modulations thereof.

In the present invention, "gene product" has a meaning generally understood in the art and specifically refers to, for example, the transcription products, the translation products, and modulations thereof.

In the present invention, "unusual alternative splicing" has a meaning generally understood in the art and specifically refers to, for example, abnormality in alternative splicing in a cell, causing a state where expression ratios of alternative splicing transcription products in the transcription products differ from those in normal cells.

"Process for measuring an abundance of a transcription product in a human-derived sample" as used herein is not particularly limited as far as the abundance of the transcription product can be measured to be in such an amount that it is comparable to the abundance of the control. The process need not to be a measurement for quantitative determination. Known nucleic acid analysis methods such as a micro-array method, an RT-PCR method, a real time PCR method, a subtraction method, a differential display method, a differential hybridization method, and a cross hybridization method can be used as a measuring method (see "New Genetic Engineering Handbook"; Yodosha CO., LTD, October 2003, "The Best We Can Do-PCR Updated Utilization Manual"; Yodosha CO., LTD, October 2003) and quantitative determination methods are preferable.

"Process for measuring an abundance of a translation product in a human-derived sample" as used herein is not particularly limited as far as the abundance of the translation product can be measured to be in such an amount that it is comparable to the abundance of the control. The process need not necessarily be a measurement for quantitative determination. Known immunological methods such as a Western blotting method and an ELISA method can be used as a measuring method (see "Protein Experiment Handbook"; Yodosha CO., LTD, July 2003, "Antibody Experiment Manual"; Yodosha CO., LTD, February 2004) and quantitative determination methods are preferable.

In the present invention, to "determine a cancerous conditions of a sample", the abundance of the measured gene products, transcription products, and translation products in the sample can be evaluated as a difference in abundance of the same product and also may be relatively or statistically evaluated as relative to the abundance with other types of products.

Specifically, for example, RNA is extracted from a sample and its control sample and the extracts are subjected to cDNA amplification for splice variant transcription product of human PTCH1 gene, i.e., the gene marker of the present invention, using a known method such as RT-PCR. The amplified cDNAs are developed on agarose gel electrophoresis, and gel stained with a dye such as ethidium bromide or fluorescent dye such as SYBR Green I to obtain a stained image. Then the stained image is compared by visual observation or digitized values obtained by digitizing the image information processing are compared to evaluate a difference in abundance. Semiquantitative amplification of the cDNA by a known real time PCR method enables comparison of abundances without agarose gel electrophoresis and analysis of stained image.

When many products are measured their abundance simultaneously by, for example, a DNA micro-array method and abundances of various types of products make a pattern relative to the abundance of each product and evaluated, splice variant product of human PTCH1 gene, i.e., the gene marker of the present invention is subjected to that evaluation to obtain relative or statistical evaluation thereof.

Further, the above-mentioned abundance can be evaluated by, for example, preparing a specific antibody to a translation product of the splice variant product of human PTCH1 gene, i.e., the gene marker of the present invention by a known method, extracting proteins from a sample and a control sample, detecting the abundances thereof by an immunological method such as the known Western blotting method or ELISA method, and evaluating the abundances.

When evaluating the above-mentioned abundances in the present invention, they can be evaluated relative to a standard value set in advance, or they can be evaluated by comparing with the abundance of the control sample set each time. In this case, as "standard value set in advance", for example, a statistic value from a plurality of samples of living body sample, normal tissue, or normal cell from healthy subject that can be used.

The present invention enables evaluation of the abundance by setting the above-mentioned standard or control respectively for various cancers, which is optimized each time.

As described above, in the present invention, the origin of the human-derived sample or its control sample is not particularly limited. In particular, samples extracted from colon, leukocyte, brain or lung are preferably used since they exhibit a good correlation between an increase in the abundance of the splice variant transcription product 1 described below of human PTCH1 transcription product and canceration of cells.

The base sequence information on human PTCH1 gene used as a marker gene in the present invention is available from a gene information database organization such as GenBank database, etc. For example, under GenBank Accession No. AL161729, a registration number of GenBank database, 189643-base long human genome DNA fragment is described and PTCH1 gene represented by bases number 52303 to 116745 is described to be constituted by 64443-base long DNA.

Further, under Genbank Accession No. NM000264 according to information on the base sequence of PTCH1 gene coded on the genome as described above, there is described a base sequence of cDNA having a length of total 6825 bases experimentally obtained using a mature mRNA existing in a cell from living body as a template, the mature mRNA in the cell from living body being obtained by transcription and splice and the human PTCH1 gene is described to be a structural gene encoding a 1447-amino acid long polypeptide.

Therefore, these information indicate that existence of an exon-intron structure having 24 exons as schematically illustrated in FIG. 1 as a structure of the transcription product transcribed from human PTCH1 gene. The cDNA described under Genbank Accession No. NM000246 is constituted by exon 1B type while reported transcription products transcribed from human PTCH1 gene include isoforms constituted by exon 1 and exon 1A type whose start codons are located at different positions (see GenBank Accession No. U43148, No. AB189440).

The human PTCH1 gene used in the present invention includes besides the gene having the above-mentioned known base sequence, those genes having in the base sequence thereof deletion, substitution and/or addition as a result of naturally occurring mutation due to a difference among individuals, a difference among organs, and a difference among tissues and so on.

In the present invention, a new alternative splicing joining site, besides the alternative splicing joining site shown in the following examples, may be explored by known methods pursuant to the following Examples 1 and 2, and based on the obtained information, a probe or its chemical modulations can be designed, which are used for measuring abundance in a human-derived sample of a gene product whose expression amount varies by abnormal alternative splicing out of gene products derived from human PTCH1 gene contained in the sample.

In the present invention, "base sequence having an ability to hybridize under stringent conditions" has a meaning generally understood in the art and refers to a polynucleotide obtained by a hybridization method such as a Southern blot hybridization method, a colony hybridization method, or a plaque hybridization method using a DNA probe. Specifically, "base sequence having an ability to hybridize under stringent conditions" refers to a polynucleotide that can be identified by hybridization at 65° C. in the presence of 0.7 to 1.0 M NaCl using a DNA immobilized on a filter, and then washing the filter at 65° C. using a 0.1 to 2 fold concentration of SSC (1×SSC; 150 mM sodium chloride, 15 mM sodium citrate) solution. The hybridization can be performed pursuant to the method described, for example, Molecular Cloning: A Laboratory Manual, Second Edition (Plainview, N.Y.: Cold Spring Harbor Laboratory Press (1989)).

Specifically, base sequences having deletion, substitution and/or insertion of one to several bases in SEQ ID Nos. 1 to 4 and having homology of at least 65%, preferably 80% or more, and more preferably 90% or more may be exemplified.

Molecular biological techniques such as RNA extraction, cDNA synthesis, DNA amplification, DNA cloning, and DNA sequencing as well as immunological techniques such as Western blotting and ELISA can be performed pursuant to those methods commonly used by one skilled in the art.

In the present invention, polynucleotides and polyribonucleotides can be chemically synthesized by a known method (see "New Genetic Engineering Handbook"; Yodosha CO., LTD, October 2003). Antibodies can be prepared by a known method that involves immunizing an animal such as rabbit, rat, and mouse with a polypeptide and using antiserum derived from the animal.

In the present invention, chemical modification for obtaining chemical modulations of a probe is not particularly limited and can be performed with a fluorescent substance, a radioisotope, an enzyme, etc. which are used by one skilled in the art for detecting trace substances.

EXAMPLE

Hereinafter, the present invention is described concretely by examples. However, the present invention should not be considered to be limited thereto.

In Examples 1 and 2 below, various cancer-derived cell lines are used to detect human PTCH1 gene splice variant transcription product, one of Hedgehog signaling genes. That is, regarding human PTCH1 gene-derived transcription products expressed in cells, expression screening of splice variant transcription product expressed besides the main transcription product thereof was performed. Here, cancer-derived cell lines used in the expression screening include HL60RG, NB4, Raji, Daudi, U937, and K562 derived from leukemia cell; ON776, TE671, D283, Daoy, Uw228, and PFSK derived from brain tumor cell; MKN1, MKN7, MKN28, MKN45, MKN74, NEDATE, KATOIII, and HSC64 derived from gastric cancer cell; SW1116 and C-1 derived from colon cancer cell; Lu65 derived from lung cancer cell; A431 derived from skin cancer cell; and PSN1, YPK1, YPK2, S2-013, Aspc1, MIApaca2, Bxpc3, H48N, KP2, KP3, KP4, KP1NL, KP1N, QGP1, and PANC1 derived from pancreas cancer cell.

Example 1

RNA Extraction

DNase Treatment

Given that extraction of total RNA from cultured cells could be performed by a commonly used method as a molecular biological method as described above, in present Example 1, RNA extraction reagent (trade name "ISOGEN-LS"; manufactured by Nippon Gene Co., Ltd.) was used to extract total intracellular RNA from 0.25 ml each of cultured cell suspension of various cancer-derived cell lines.

Specifically, to 0.25 ml of cultured cell suspension containing 0.5 to $5.0 \times 10^5$ cells suspended in 1×PBS buffer in advance, 0.75 ml of an RNA extraction reagent (trade name "ISOGEN-LS"; manufactured by Nippon Gene Co., Ltd.) was added. After the resultant mixture was left at room temperature for 5 minutes, 0.2 ml of chloroform was added thereto and the mixture was vigorously vortexed for about 15 seconds. The obtained solution was left at room temperature for 2 to 3 minutes and then centrifuged at 12,000×g at 4° C. for 10 minutes to obtain a liquid-liquid phase separated solution having a lower layer of an organic solvent phase, a medium layer and an upper layer of aqueous phase. Among these layers, the aqueous phase containing RNA was carefully extracted. An equal amount of isopropanol was added to the aqueous phase solution and mixed. The mixture was centrifuged at 12,000×g at 4° C. for 15 minutes to precipitate RNA, and the RNA pellet was washed with 1 ml of 75% ethanol. After removal of the supernatant and air-drying, the pellet was dissolved in 50 µl of TE buffer (10 mM Tris-HCl, 0.1 mM EDTA, pH 8.0). The obtained RNA was measured for optical density at 260 nm (OD260) using a spectrophotometer (trade name "Gene Quant pro "S"; Amasham Bio Science Co., Ltd.), and the concentration of RNA was determined by converting 1 $OD_{260}$ to 40 µg of RNA.

By this method, though somewhat varying depending on respective cell lines and experimental conditions, RNA could be obtained in a yield of 5.0 µg to 30 µg from 0.25 ml of cultured cell suspension containing 0.5 to $5.0 \times 10^5$ cells.

The RNA solution thus obtained is a solution from which contaminants derived from cells such as DNA and proteins are excluded to a considerable extent. However, to exclude potential influence of DNA remaining in minute amounts, DNase treatment was performed using a DNase treatment kit (trade name "RQ1 RNase-Free DNase kit"; manufactured by Promega Corp.) Specifically, RNA solution correspond to 3 µg of RNA was dispensed into a Nuclease-free tube from the quantitated RNA solution and 3 µl each of 10× reaction mixture and DNAase solution (1 unit/µl) which were reagents attached to the kit were added, and then Nuclease-free $H_2O$ was added to make a total liquid amount of 30 µl, thereby providing a reaction mixture. This reaction mixture was incubated at 37° C. for 30 minutes to allow DNase enzyme reaction to proceed. Thereafter, 3 µl of reaction termination solution attached to the kit was added to the reaction mixture to stop the reaction and then the resultant was incubated at 65° C. for 10 minutes to inactivate the DNase.

Example 2

RT-PCR

Agarose Electrophoresis

Specific amplification of a DNA fragment having a specified sequence from the total RNA extracted from cultured cell or the like can be performed pursuant to the known RT-PCR method as described above. In present Example 2, the amplification was performed using an RT-PCR kit (trade name "Rever Tera Ace-α-kit"; manufactured by Toyobo Co., Ltd.) for cDNA amplifications, thermotolerant DNA polymerase for PCR (trade name "Ampli Taq Gold"; Applied Biosystems, U.S.A.), and a reaction reagent therefor (trade name "10× PCR Gold buffer"; Applied Biosystems, U.S.A.) as a PCR reaction reagent after cDNA amplification.

Figure 2:
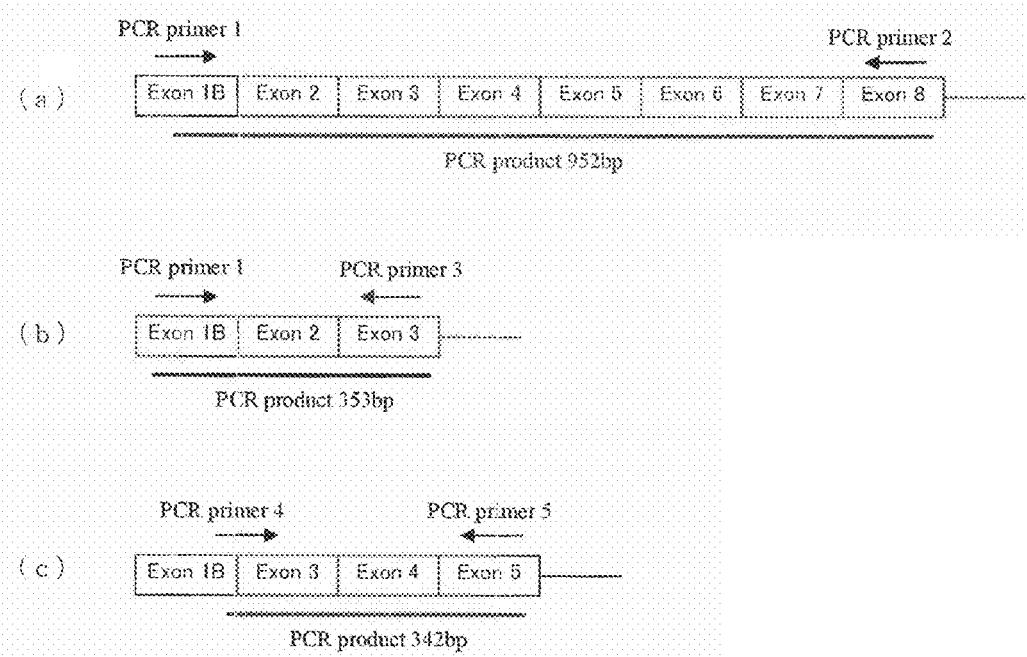
FIG. 2 A schematic diagram illustrating PCR primer site designed for amplifying a partial sequence of a transcription product of human PTCH1 gene.

As PCR primers, PCR primer 1 (SEQ ID No. 5) and PCR primer 2 (SEQ ID No. 6) were designed at primer site as shown in FIG. 2(a) based on the base sequences present in exon 1B and exon 8 on the human PTCH1 gene. Then, by reverse transcription PCR (RT-PCR) using the primer set, a DNA fragment having a base sequence of 952-base long was amplified as a transcription product derived from human PTCH1 gene contained in the total RNA extracted from the cultured cells.

Specifically, an amount of RNA solution, adjusted to 1 μg/μl, corresponding to 1 μg RNA subjected to the above-mentioned DNase treatment and reagent solutions attached to the RT-PCR kit were mixed in amounts described below, and Nuclease-free H$_2$O was added to make a total liquid amount 30 μl to provide a reaction mixture for reverse transcription. This was subjected to first strand cDNA synthesis by reverse transcriptase reaction under conditions of (30° C., 10 minutes)→(42° C., 20 minutes)→(99° C., 5 minutes)→(4° C., 5 minutes). Here, the random primer is 5'-(dN)9-3', and Rever-Tra Ace is a reverse transcriptase having an ability to synthesize cDNA. In this, a single strand DNA having a sequence complementary to RNA (1st strand cDNA) is synthesized in the form of a mixture of products by using the random primer.

Reverse Transcription Reagent Solution

5×RT Buffer 4 μl
dNTP Mixture (10 mM) 2 μl
RNase Inhibitor (10 U/μl) 1 μl
Random Primer (25 pmol/μl) 1 μl
ReverTra Ace 1 μl Then, 1 μl of the reaction solution obtained in the reverse transcriptase reaction and a PCR reaction reagent solution were mixed in amounts described below and Nuclease-free H$_2$O was added to make a total liquid amount 26 μl to provide a reaction mixture for PCR reaction. This was subjected to PCR reaction under conditions of (94° C., 10 minutes)→denaturation (94° C., 1 minute)→annealing (60° C., 1 minute) →elongation (72° C., 1 minute 30 seconds)→(72° C. 7 minutes)→(4° C.). The PCR cycle of denaturation, annealing, and elongation reactions was set to 40 cycles.

PCR Reaction Regent Solution

10×PCR Gold buffer 2.5 μl
MgCl$_2$ (25 mM) 1.5 μl
2 mM dNTP mixture 2.5 μl
PCR primer 1 (10 pmol/μl) 0.625 μl
PCR primer 2 (10 pmol/μl) 0.625 μl
Ampli Tag Gold (5 U/μl) 0.15 μl
DNA Sequence:
PCR primer 1 (SEQ ID NO: 5)
PCR primer 2 (SEQ ID NO: 6)

Figure 3:
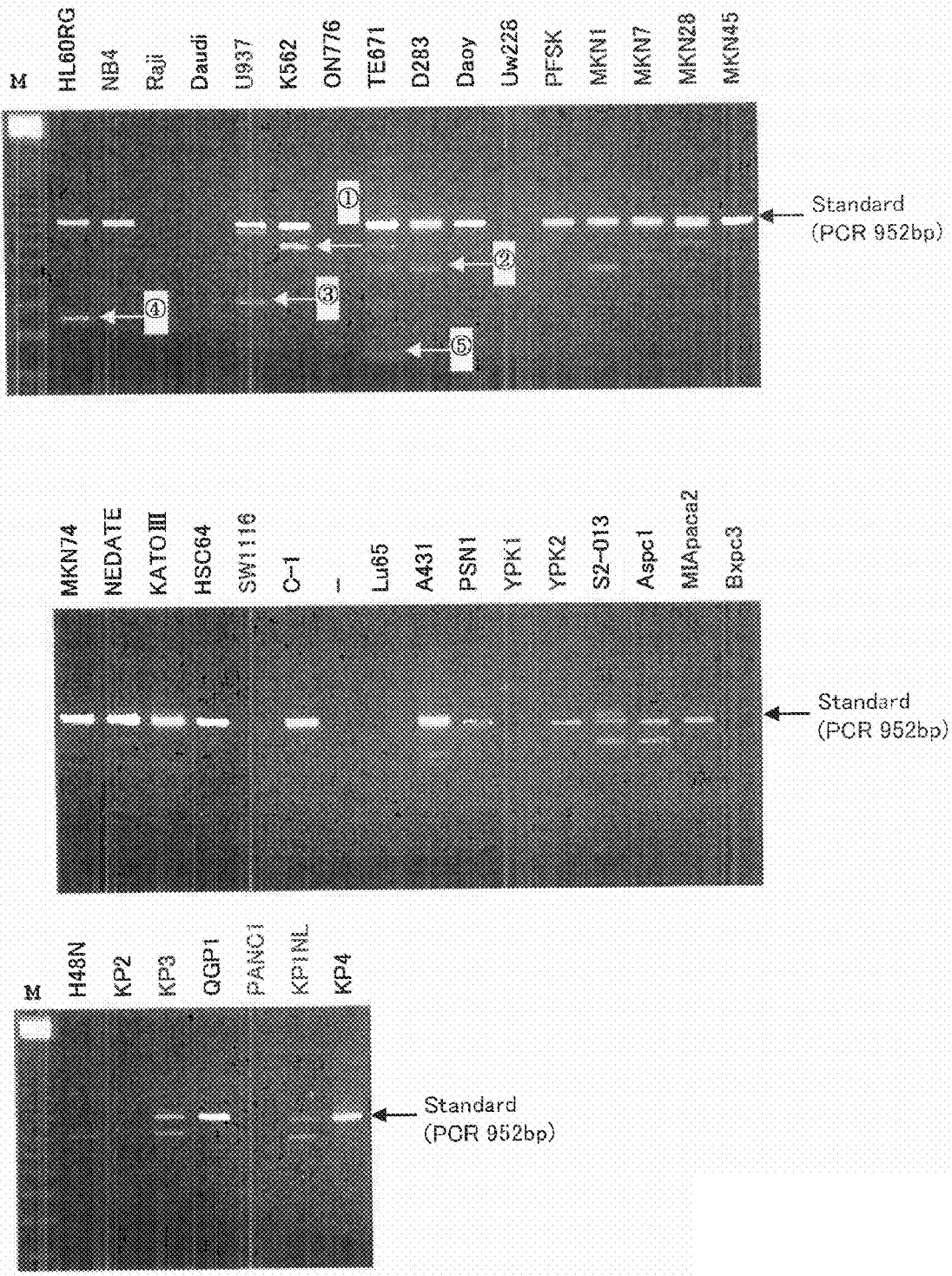
FIG. 3 A photograph of agarose electrophoresis indicating result of amplification of partial sequences of transcription products of human PTCH1 gene by RT-PCR with RNAs extracted from various cancer-derived cell lines.

A portion of solution after the PCR reaction was electrophoresed on 1.5% agarose gel (TAE buffer: 40 mM Tris, 19 mM acetic acid, 1 mM EDTA) and the resultant gel was stained with a 0.5 μg/ml ethidium bromide aqueous solution. FIG. 3 is a photograph of the electrophoresis when irradiated with UV rays. In FIG. 3, the lane M stands for a nucleic acid molecular weight marker and other lanes stand for electrophoresis of amplified DNA fragments using the PCR primer set consisting of PCR primer 1 (SEQ ID No. 5) and PCR primer 2 (SEQ ID No. 6) from the total RNA extracted from respective cultured cells of various cancer-derived cell lines used in expression screening.

As indicated by arrow 1 in FIG. 3, DNA fragments detected by RT-PCR of transcription products from human PTCH1 gene extracted from cultured cells of cell line K562 include a 952-base long fragment anticipated from the full-length transcription product thereof and a DNA fragment at a position in the vicinity of 760-base length using the mobility of the nucleic acid molecular weight marker (lane M). The DNA fragment in the vicinity of 760-base length was also detected in RNAs from cell lines TE671, MKN28, S2-013, Aspc1, H48N, KP3, and KP1NL.

Also, as indicated by arrow 2 in FIG. 3, DNA fragments detected by RT-PCR of transcription products from human PTCH1 gene extracted from cultured cells of cell line D283 include a 952-base long portion anticipated from the full-length transcription product thereof and a DNA fragment at a position in the vicinity of 550-base length using the mobility of the nucleic acid molecular weight marker (lane M). The DNA fragment in the vicinity of 550-base length was also detected in RNAs from cell lines TE671 and MKN1.

Further, as indicated by arrows 3 to 5 in FIG. 3, DNA fragments were detected at positions in the vicinity of 380-, 250- and 150-base length from RNAs extracted from cultured cells of cell lines U937, HL60RG, and TH671, respectively. Also, DNA fragments were detected at positions in the vicinity of 380- and 150-base length from RNAs extracted from cultured cells of cell line KP4. Besides the above-mentioned DNA fragments, further DNA fragments were detected at a position in the vicinity of 250-base length from RNAs extracted from cultured cells of cell line TE671.

These DNA fragments were sequence-specifically synthesized by amplification from transcription products derived from human PTCH1 gene contained in the total RNA extracted from cultured cells or the like by RT-PCT using a primer set of PCR primer 1 (SEQ ID No. 5) and PCR primer 2 (SEQ ID No. 6). This suggested that presence of splice variant transcription products of human PTCH1 gene corresponding to the above-mentioned DNA fragments detected at the positions in the vicinity of 760-, 550-, 380-, 250-, and 150-base length.

Example 3

Identification of Splice Variant Transcription Products

To confirm whether or not the four DNA fragments detected at positions in the vicinity of 760-, 550-, 380-, and 250-base length, respectively, are amplification and synthesis products from splice variant transcription products of human PTCH1 gene and to determine base sequences thereof, the bands indicated by arrows 1 to 4 in FIG. 3 were cut out and the base sequences of the detected DNA fragments were confirmed by cloning and DNA sequencing. Specifically, the following methods were used.

First, four types of DNA bands developed by electrophoresis on 1.5% agarose gel were cut out and DNAs were extracted therefrom using gel band extraction kit (trade name "MinElute Gel Extraction kit"; manufactured by Quiagen Co., Ltd.).

Specifically, the cut out gel slice (0.1 to 0.3 mg) was put in a 1.5-ml tube, an about 3-volumes (for example, 300 μl for 100 mg) of buffer QG attached to the kit was added to the gel slice. The mixture was incubated at 50° C. for 10 minutes to dissolve the gel and then isopropanol in the same amount as the gel was added, followed by turning the tube upside down to mix the solution. MinElute column attached to the kit was placed in a 2-ml collection tube, a sample was applied to the column and the column was centrifuged at 10,000×g for 1 minute to discard flow-through liquid and allow DNA to be adsorbed by the column. For washing, 750 μl of Buffer PE attached to the kit was added to the column. After being left to stand for 5 minutes, the flow-through liquid was discarded by centrifugation at 10,000×g for 1 minute and further centrifugation was performed at 10,000×g for 1 minute to discard ethanol derived from Buffer PE completely. The thus treated column was charged in a new 1.5-ml tube and 10 μl of Buffer EB attached to the kit was added to the center of the column membrane. After being left to stand for 1 minute, the column was centrifuged at 10,000×g for 1 minute to elute DNA. An average elution amount was about 9 μl.

While cloning of the DNA extracted from the agarose gel into a DNA vector can be performed by a method commonly used as a molecular biological technique as mentioned above, in present Example 3, a DNA cloning kit (trade name "TOPO cloning Reaction"; manufactured by Invitrogen Co., Ltd.) was used.

Specifically, to 2 μl of the DNA eluate extracted from the gel slice were added 1 μl of Salt Solution, a reagent solution attached to the kit, 1 μl of TOPO vector, and 2 μl of sterilized water and the resultant mixture was left to stand at room temperature for 5 minutes. The mixture was transferred on ice and 2 μl of the mixture was added to 50 μl of *Escherichia coli* competent cell (trade name "One Shot Chemically Competent *E. coli*"; manufactured by Invitrogen Co., Ltd.), and gently suspended. The suspension was incubated on ice for 30 minutes and then at 42° C. for 30 seconds. Immediately, the incubated mixture was transferred on ice, 250 μl of S.O.C. medium was added to the mixture, and the resultant mixture was shaken at 200 rpm at 37° C. for 60 minutes. The emulsion of the bacterium was spread on an LB agar plate (containing 100 μg/ml ampicillin) which was preliminarily coated and thus impregnated with 32 μl of 50 mg/ml X-gal (5-bromo-4-chloro-3-indolyl-β-D-galactopyranoside) and 50 μl of 0.1 M IPTG (isopropyl-β-thiogalactopyranoside). Then, the bacterium was cultured at 37° C. for 12 hours. White colonies that emerged were picked up and further cultured in 2 ml of LB medium for 16 hours.

The *E. coli* thus isolated was subjected to a commonly used alkali-SDS method to extract *E. coli* plasmid vector and whether or not the insert DNA is present at an exogenous gene insertion site of the TOPO vector was confirmed. That is, using a PCR primer set of M13-20 Forward (SEQ ID No. 10) and M13-20 Reverse (SEQ ID No. 11) based on the sequence in the vicinity of the exogenous gene insertion site, PCR reaction was performed under the same conditions as that in Example 2 except for the PCR primer set and the obtained PCR product was electrophoresed to develop on 1.5% agarose gel and whether or not a DNA fragment having an expected base length was inserted was confirmed.

While determination of base sequence of the DNA fragment cloned into the DNA vector could be performed pursuant to a commonly used molecular biological technique as mentioned above, in present Example 3, a DNA sample for DNA sequencing was prepared from a PCR product using a PCR product sequencing kit (trade name "PCR Product Pre-Sequencing kit"; manufactured by USB Corp. U.S.A.) and sequencing reaction was performed using a thermal cycle sequencing kit (trade name "BigDye Terminator Cycle Sequencing kit"; manufactured by Applied Biosystems Corp. U.S.A.).

Specifically, a DNA fragment cloned into TOPO vector, an *E. coli* plasmid, was subjected to PCR reaction using the PCR primer set of M13-20 Forward (SEQ ID No. 10) and M13-20 Reverse (SEQ ID No. 11) under the same conditions as that in Example 2 except for the PCR primer set. To 5 μl of the PCR product were added reagent solutions attached to the kit, 1 μl of Exonuclease I (10 U/μl) and 1 μl of Shrimp Alkaline Phosphatase (2 U/μl), to form a pre-sequencing reaction mixture. The pre-sequencing reaction mixture (7 μl) was incubated under conditions of (37° C., 15 minutes) (80° C., 15 minutes) to enzymatically decompose and remove the primer. To 3 μl of the primer-removed sample, 3 μl of a sequencing primer (1 pmol/μl), 6 μl of sterilized water, and 8 μl of a reagent solution attached to the thermal cycle sequencing kit, Terminator premix, were dispensed in a PCR tube to form a sequencing reaction mixture. The sequencing reaction mixture (20 μl) was incubated by a cycle of denaturation (96° C., 10 seconds)→annealing (50° C., 5 seconds)→elongation (60° C., 4 minutes)→(4° C.). Note that the sequencing primers used include the above-mentioned PCR primer 1 (SEQ ID No. 5) and pCR primer 2 (SEQ ID No. 6), which were provided for sequencing reactions from the 5'- and 3'-sides, respectively. The thermal cycle of denaturation, annealing, and elongation reaction were performed in 25 cycles and the solution after the reaction was mixed with 3 μl of 3 M sodium acetate (pH 4.6), 62.5 μl of 95% ethanol, and 14.5 μl of sterilized water and the resultant mixture was left to stand at room temperature for 15 minutes. Then, the mixture was centrifuged at 14,000 rpm for 20 minutes to precipitate DNA. The DNA pellet were washed with 0.25 ml of 75% ethanol. After removing the supernatant and air-drying the pellet, 25 μl of a reagent solution HiDi attached to the thermal cycle sequencing kit was added and incubated at 95° C. for 2 minutes. After the incubation, the mixture was cooled on ice water for about 30 minutes and base sequence of the obtained DNA was determined using a DNA sequencing apparatus (trade name "310 Genetic Analyzer"; Applied Biosystems Corp. U.S.A.).

Figure 4:
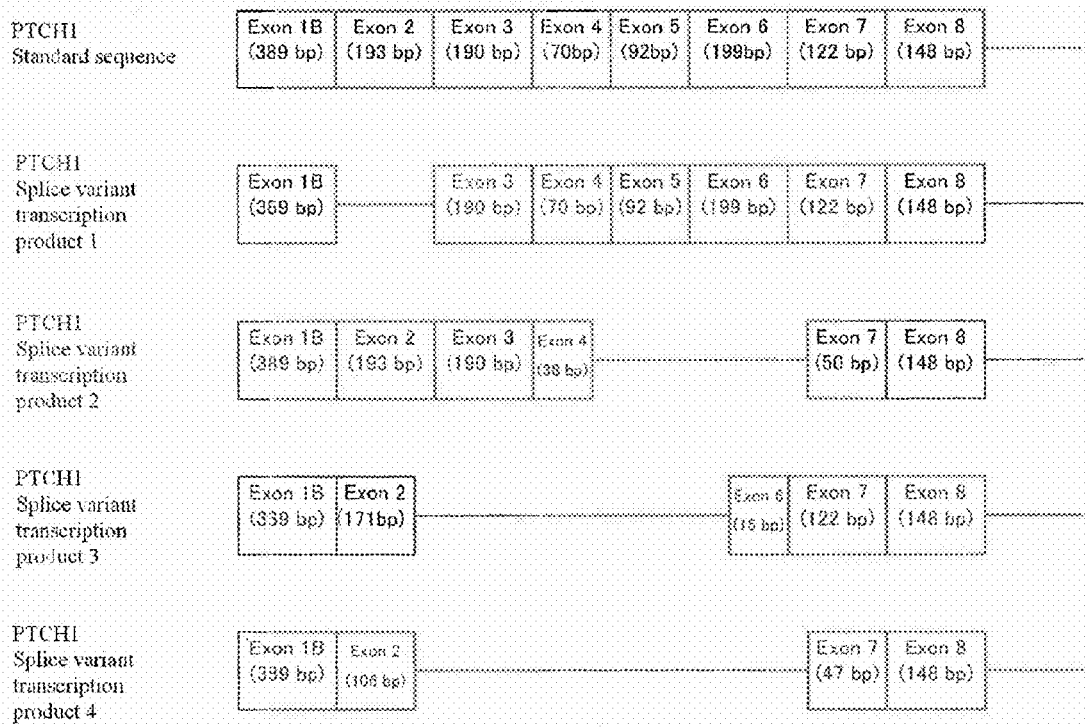
FIG. 4 A schematic diagram illustrating structures of PTCH1 splice variant transcription products 1 to 4 identified as transcription products of human PTCH1 gene.

As a result, the four DNA fragments detected at positions in the vicinity of 760-, 550-, 380-, and 250-base length revealed to be 759, 557, 394, and 239 base-long DNA fragments having base sequences of SEQ ID Nos. 13 to 16, respectively. FIG. 4 schematically shows structure thereof. Note that a corresponding portion of cDNA from the transcription product having a standard sequence not subjected to alternative splicing (952 base long) had a base sequence shown in SEQ ID No. 12.

As shown in FIG. 4, these DNA fragments had a structure in which exons were partly dropped from the transcription product of human PTCH1; splice variant transcription product 1 in which exon 2 portion (193 bp) was deleted from the transcription product of human PTCH1 gene, splice variant transcription product 2 in which a portion from halfway of exon 4 to halfway of exon 7 was deleted, splice variant transcription product 3 in which a portion from halfway of exon 2 to halfway of exon 6 was deleted, and splice variant transcription product 4 in which a portion from halfway of exon 2 to halfway of exon 7 was deleted were confirmed.

Example 4

Among the splice variant transcription products 1 to 4 of human pTCH1 gene newly identified in Example 3 above, the splice variant translation product 1 was selected and an oligonucleotide primer for detecting the splice variant translation product 1 specifically and with high sensitivity was designed. That is, as shown in FIG. 2(c), an oligonucleotide primer, i.e., PCR primer 4 (SEQ ID No. 8), was designed which has sequence specific binding ability to a structure in which exon 1B and exon 3 are joined based on the base sequence of the alternative splice joint portion of the splice variant transcription product 1.

To confirm usability of the oligonucleotide primer, PCR primer 4 (SEQ ID No. 8), a primer set of PCR primer 4 and PCR primer 5 (SEQ ID No. 9) was formed and RT-PCR was performed in the same manner as that in Example 2 except that the PCR primer set was different. From this method expression of the splice variant transcription product 1 in cancer-derived cell lines used in screening above and KP1N derived from a pancreas cancer cell was examined. Note that a partial sequence of β-actin transcription product was similarly synthesized by RT-PCR amplification using a primer set consisting of a PCR primer shown in SEQ ID No. 17 and a PCR primer shown in SEQ ID No. 18 to provide a control for the detection condition.

Figure 5:
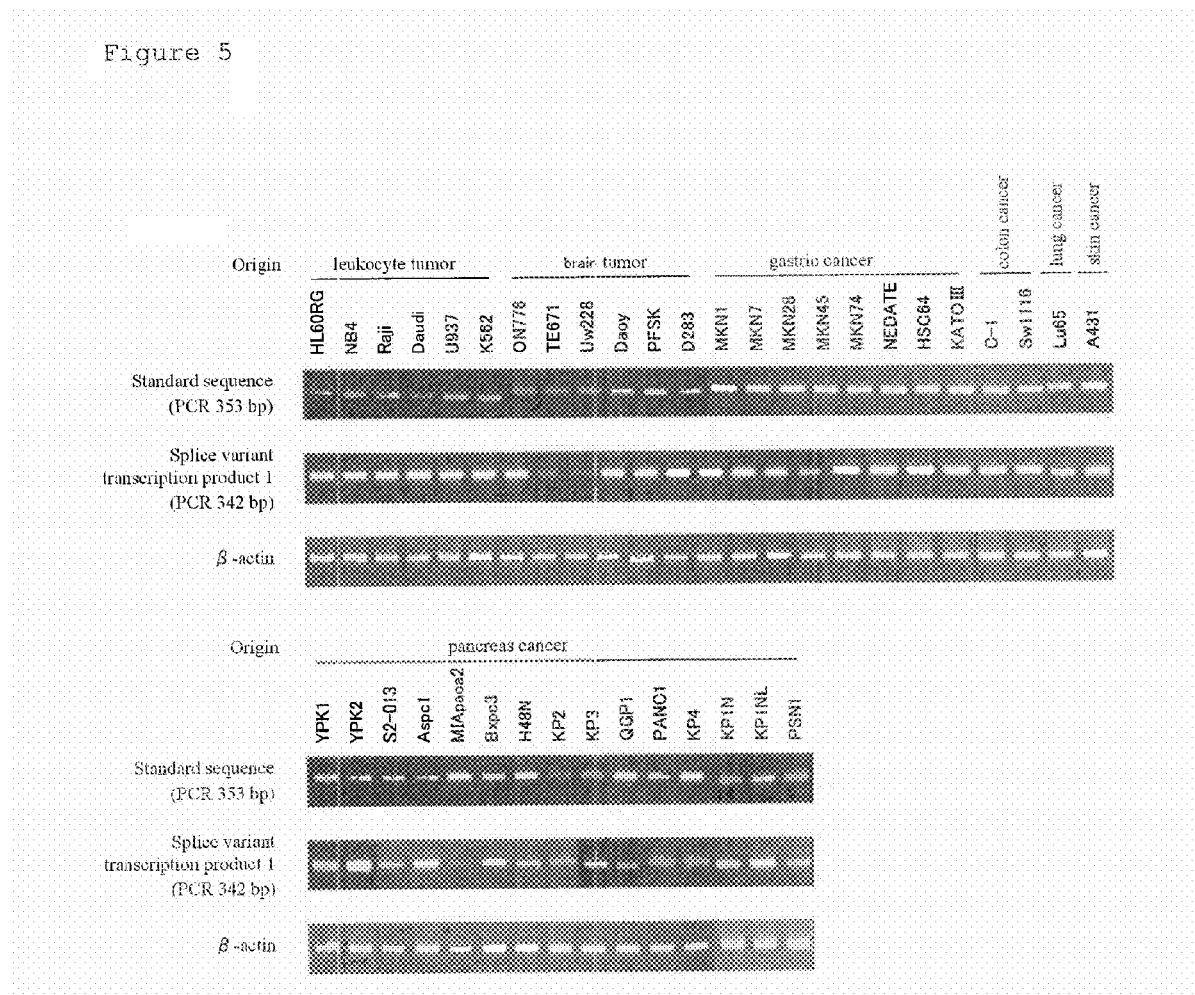
FIG. 5 A photograph of agarose electrophoresis indicating result of detection of PTCH1 splice variant transcription product 1 with PCR primer 4 (SEQ ID No. 8).

As a result, as shown in FIG. 5, it has been confirmed that splice variant transcription product 1 was detected in all the cancer-derived cell lines and PCR primer 4 (SEQ ID No. 8) was useful as an oligonucleotide primer for detecting the splice variant transcription product 1 of human PTCH1 gene specifically and with high sensitivity. Note that by using the primer set consisting of PCR primer 1 (SEQ ID No. 5) and PCR primer 3 (SEQ ID No. 7), the transcription products having a standard sequence not having been subjected to alternative splicing were confirmed to be expressed in all the cancer-derived cell lines.

Example 5

Among the splice variant transcription products 1 to 4 of human PTCH1 gene newly identified in Example 3 above, the splice variant translation product 1 was examined whether to be useful as a cancer marker for distinguishing cancer cells from normal cells.

First, expression in various normal tissues was compared. For this purpose, with a commercially available panel normal tissue cDNA (manufactured by BD Biosciences Corp.), human normal tissues such as heart, brain, placenta, lung, liver, skeletal, kidney, pancreas, spleen, thymus, prostate, testis, ovary, small intestine, colon, and leukocyte were detected for splice variant transcription variant 1 using a primer set same with that in Example 4.

As a result, as indicated by the photograph of gel staining shown in FIG. 6(a) and relative comparison of degrees of staining of bands as shown in FIG. 6(b), no or only weak expression of the splice variant transcription product 1 was observed for human normal tissues such as heart, brain, placenta, lung, skeletal, thymus, prostate, ovary, small intestine, colon, and leukocyte. This indicates that for these tissues, there is the possibility that a cancerous conditions can be determined using abundance of the splice variant translation product 1 as an index.

Figure 6:
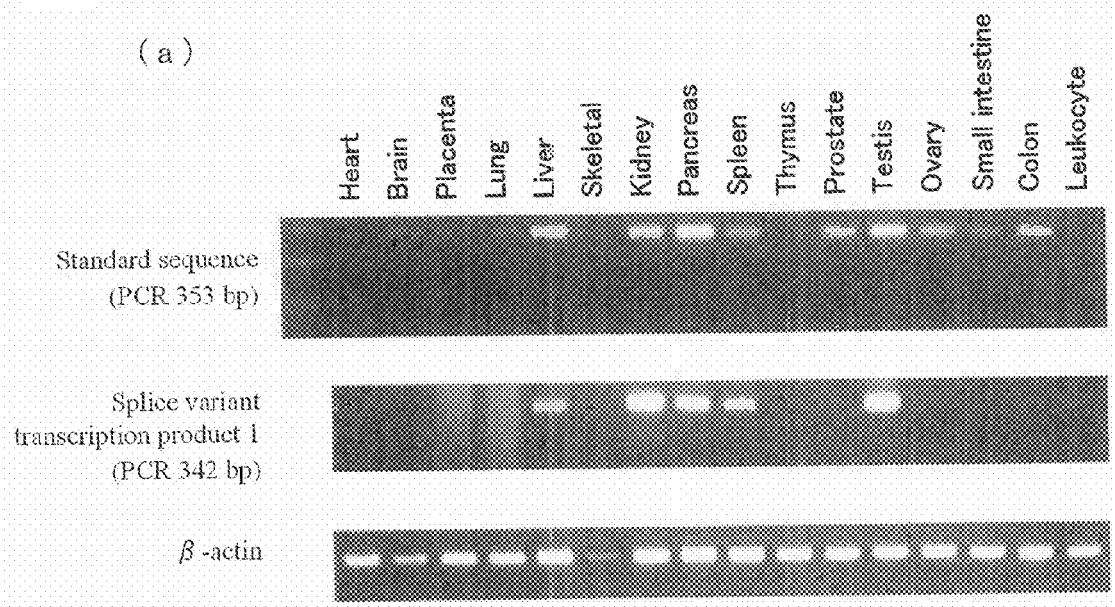
FIG. 6 A photograph of agarose electrophoresis indicating result of detection of a PTCH1 splice variant transcription product 1 with PCR primer 4 (SEQ ID NO. 8) in relation to RNAs extracted from various normal tissues.

In particular, brain, placenta, lung, prostate, ovary, small intestine, and colon in FIG. 6, there was the difference between the expression amount of the translation product having a standard sequence not having been subjected to alternative splicing and the expression amount of the splice variant transcription product 1. Further, among them, prostate, ovary, small intestine, and colon exhibited a significant difference, which suggested that not only the abundance of the splice variant translation product 1 but also a difference between such an abundance and the expression amount of the transcription product having a standard sequence not having been subjected to alternative splicing may be used as an index.

On the other hand, as will be apparent from comparison between the results on cancer cells shown in FIG. 5 and the results on normal cells shown in FIG. 6, in at least colon, leukocyte, brain, and lung, the abundance of the splice variant transcription product 1 is significantly different between the normal cells and the cancer cells. This indicates that the splice variant transcription product 1 is useful as a cancer marker for cancers derived from these tissues.

Figure 7:
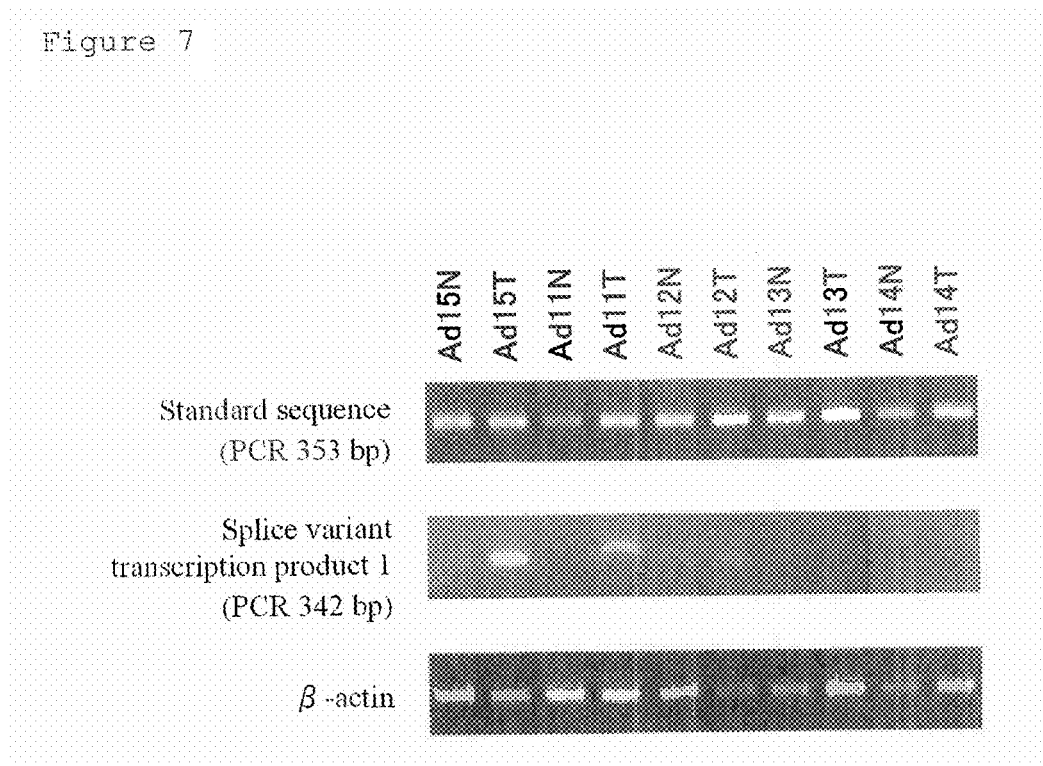
FIG. 7 A photograph of agarose electrophoresis indicating result of detection of a PTCH1 splice variant transcription product 1 with PCR primer 4 (SEQ ID NO. 8) in relation to RNA extracted from a tissue of colon from a patient with colon cancer.

Then, RNAs extracted by a guanidine-acidic phenol method from 25 samples of normal tissue (N) and cancer tissue (T) of colon tissue sections from subjects with colon cancer were examined for their expression of the splice variant transcription product 1 in the same manner as that in Example 4. FIG. 7 shows a part of the results as a photograph of gel staining of the splice variant transcription product 1 and relative comparison of degree of staining of bands on the whole is shown in Table 1 below. Note that the results on colon tissue sections from the same subject are indicated with the same number symbols.

TABLE 1

| Normal tissue | Standard | Variant exon2 deletion | β-actin | Cancer tissue | Standard | Variant exon2 deletion | β-actin |
|---|---|---|---|---|---|---|---|
| 7N | + | + | + | 4T | + | + | + |
| 22N | + | + | + | 8T | + | + | + |
| 23N | + | − | + | 9T | + | + | + |
| 24N | + | + | + | 10T | + | + | + |
| 27N | + | + | + | 15T | + | + | + |
| 32N | + | − | + | 16T | + | − | + |
| 35N | + | − | + | 18T | + | + | + |
| 43N | + | − | + | 21T | + | + | + |
| 61N | + | − | + | 23T | + | + | + |
| 64N | + | − | + | 43T | + | − | + |
| 71N | + | − | + | 64T | + | − | + |
| 86N | + | − | + | 86T | + | + | + |
| 88N | + | − | + | 102T | + | + | + |
| 94N | + | − | + | 116T | + | − | + |
| 95N | + | − | + | 128T | + | + | + |
| 102N | + | − | + | 154T | + | + | + |
| 125N | + | − | + | 155T | + | + | + |
| 127N | + | − | + | 181T | + | − | + |
| 128N | + | − | + | 182T | + | +/− | + |
| 190N | + | − | + | 190T | + | +/− | + |

TABLE 1-continued

| Normal tissue | Standard | Variant exon2 deletion | β-actin | Cancer tissue | Standard | Variant exon2 deletion | β-actin |
|---|---|---|---|---|---|---|---|
| Ad11N | + | − | + | Ad11T | + | + | + |
| Ad12N | + | +/− | + | Ad12T | + | + | + |
| Ad13N | + | − | + | Ad13T | + | − | + |
| Ad14N | + | − | + | Ad14T | + | − | + |
| Ad15N | + | − | + | Ad15T | + | + | + |

※T = tumor, N = normal; The number represents for each subject.

As shown in FIG. 7, a significant difference in expression of the splice variant transcription product 1 was observed between normal tissues (N) and cancer tissues (T) from subjects Ad11, Ad12, and Ad15. Further, although not shown in Figures as photograph, similar results were obtained for subject numbers 23, 86, 102, 128, and 190. The cancerous conditions of these tissue sections or cells that constitute the tissue sections could be determined.

As shown in Table 1, expression of the splice variant transcription product 1 was observed in 5 samples out of 25 samples (20%) in normal tissues (N) while in cancer tissues (T), the splice variant transcription product 1 was expressed in high frequency, specifically in 18 samples out of 25 samples (72%). This suggested that the splice variant transcription product 1 is useful for determining a cancerous conditions.

Free Text of Sequence List

SEQ ID NO 1: base sequence of alternative splicing joining part of transcription product 1 caused by splice variant transcription product of human PTCH1 gene SEQ ID NO 2: base sequence of alternative splicing joining part of transcription product 2 caused by splice variant transcription product of human PTCH1 gene SEQ ID NO 3: base sequence of alternative splicing joining part of transcription product 3 caused by splice variant transcription product of human PTCH1 gene SEQ ID NO 4: base sequence of alternative splicing joining part of transcription product 4 caused by splice variant transcription product of human PTCH1 gene SEQ ID NO 5: PCR primer 1 for amplifying a partial sequence of transcription product of human PTCH1 gene SEQ ID NO 6: PCR primer 2 for amplifying a partial sequence of transcription product of human PTCH1 gene SEQ ID NO 7: PCR primer 3 for amplifying a partial sequence of transcription product of human PTCH1 gene SEQ ID NO 8: PCR primer 4 for amplifying a partial sequence of transcription product of human PTCH1 gene SEQ ID NO 9: PCR primer 5 for amplifying a partial sequence of transcription product of human PTCH1 gene SEQ ID NO 10: DNA forward primer for PCR for amplifying DNA fragment cloned on plasmid TOPO vector SEQ ID NO 11: DNA reverse primer for PCR for amplifying DNA fragment cloned on plasmid TOPO vector SEQ ID NO 12: cDNA partial sequence of transcription product of PTCH1

SEQ ID NO 13: cDNA partial sequence of splice variant transcription product 1 of PTCH1

SEQ ID NO 14: cDNA partial sequence of splice variant transcription product 2 of PTCH1

SEQ ID NO 15: cDNA partial sequence of splice variant transcription product 3 of PTCH1

SEQ ID NO 16: cDNA partial sequence of splice variant transcription product 4 of PTCH1

SEQ ID NO 17: DNA forward primer for PCR for amplifying a partial sequence of transcription product of human β-actin gene SEQ ID NO 18: DNA reverse primer for PCR for amplifying a partial sequence of transcription product of human β-actin gene

INDUSTRIAL APPLICABILITY

According to the present invention, a simple and high-sensitive diagnostic or test method for distinguishing cancer cells from normal cells and a reagent therefor can be provided.

The invention claimed is:

1. A method of determining a colon cancer tissue in a human test patient comprising:
   obtaining a first sample from a non-cancerous human subject and a second sample from the test patient,
   measuring a transcription product of the human patched homolog 1 (PTCH1) gene comprising SEQ ID NO: 1 in the first and second sample by contacting the samples with a probe or primer that hybridizes to the splice junction in SEQ ID NO: 1 or the complement of SEQ ID NO: 1, wherein the splice junction is between exon1B and exon 3 of PTCH1, and
   comparing the level of measured transcription product from the first and second samples, wherein if the level of measured transcription product in the second sample is higher than the level of measured transcription product in the first sample, the test patient comprises a colon cancer tissue.

2. The method according to claim 1, wherein the probe or primer hybridizes to the complement of SEQ ID NO: 1.

3. The method according to claim 1, wherein the first sample, the second sample, or both is a tissue sample.

4. The method according to claim 1, wherein the method of measuring is any one of the measuring methods selected from the group consisting of a micro-array method, an RT-PCR method, a real time PCR method, a subtraction method, a differential display method, a differential hybridization method, and a cross hybridization method.

5. The method according to claim 2, wherein the probe or primer is 15 to 30 nucleotides long.

6. The method according to claim 1, wherein the probe or primer is 15 to 30 nucleotides long.

* * * * *

```
SEQUENCE LISTING

<160> NUMBER OF SEQ ID NOS: 18

<210> SEQ ID NO 1
<211> LENGTH: 20
<212> TYPE: RNA
<213> ORGANISM: Homo sapiens

<400> SEQUENCE: 1
auuuccaagu uggaggacga                                              20

<210> SEQ ID NO 2
<211> LENGTH: 20
<212> TYPE: RNA
<213> ORGANISM: Homo sapiens

<400> SEQUENCE: 2
aaucaggagg aguugauugu                                              20
```

```
<210> SEQ ID NO 3
<211> LENGTH: 20
<212> TYPE: RNA
<213> ORGANISM: Homo sapiens

<400> SEQUENCE: 3
gagaccaaca aaaauucaac                                                   20

<210> SEQ ID NO 4
<211> LENGTH: 20
<212> TYPE: RNA
<213> ORGANISM: Homo sapiens

<400> SEQUENCE: 4
aguucuuggu ugauuguggg                                                   20

<210> SEQ ID NO 5
<211> LENGTH: 20
<212> TYPE: DNA
<213> ORGANISM: Homo sapiens

<400> SEQUENCE: 5
cttcgctctg gagcagattt                                                   20

<210> SEQ ID NO 6
<211> LENGTH: 22
<212> TYPE: DNA
<213> ORGANISM: Homo sapiens

<400> SEQUENCE: 6
gaagtgctcg tacatttgct tg                                                22

<210> SEQ ID NO 7
<211> LENGTH: 20
<212> TYPE: DNA
<213> ORGANISM: Homo sapiens

<400> SEQUENCE: 7
gtaggagcgc ttctgtggtc                                                   20

<210> SEQ ID NO 8
<211> LENGTH: 20
<212> TYPE: DNA
<213> ORGANISM: Homo sapiens

<400> SEQUENCE: 8
atttccaagt tggaggacga                                                   20

<210> SEQ ID NO 9
<211> LENGTH: 20
<212> TYPE: DNA
<213> ORGANISM: Homo sapiens

<400> SEQUENCE: 9
actgtaattt cgccccttcc                                                   20

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      plasmid sequence
```

<400> SEQUENCE: 10
gtaaaacgac ggccag                                              16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      plasmid sequence

<400> SEQUENCE: 11
caggaaacag ctatgac                                             17

<210> SEQ ID NO 12
<211> LENGTH: 952
<212> TYPE: DNA
<213> ORGANISM: Homo sapiens

<400> SEQUENCE: 12
cttcgctctg gagcagattt ccaaggggaa ggctactggc cggaaagcgc cgctgtggct    60
gagagcgaag tttcagagac tcttatttaa actgggttgt tacattcaaa aaaactgcgg   120
caagttcttg gttgtgggcc tcctcatatt tggggccttc gcggtgggat taaaagcagc   180
gaacctcgag accaacgtgg aggagctgtg ggtggaagtt ggaggacgag taagtcgtga   240
attaaattat actcgccaga agattggaga agaggctatg tttaatcctc aactcatgat   300
acagacccct aaagaagaag gtgctaatgt cctgaccaca gaagcgctcc tacaacacct   360
ggactcggca ctccaggcca gccgtgtcca tgtatacatg tacaacaggc agtggaaatt   420
ggaacatttg tgttacaaat caggagagct tatcacagaa acaggttaca tggatcagat   480
aatagaatat ctttacccct tgtttgattat tacacctttg gactgcttct gggaaggggc   540
gaaattacag tctgggacag catacctcct aggtaaacct cctttgcggt ggacaaactt   600
cgaccctttg gaattcctgg aagagttaaa gaaaataaac tatcaagtgg acagctggga   660
ggaaatgctg aataaggctg aggttggtca tggttacatg gaccgcccct gcctcaatcc   720
ggccgatcca gactgccccg ccacagcccc caacaaaaat tcaaccaaac tcttgatat    780 ggccccttgtt ttgaatggtg gatgtcatgg cttatccaga aagtatatgc actggcagga   840
ggagttgatt gtgggtggca cagtcaagaa cagcactgga aaactcgtca gcgcccatgc   900
cctgcagacc atgttccagt taatgactcc caagcaaatg tacgagcact tc           952

<210> SEQ ID NO 13
<211> LENGTH: 759
<212> TYPE: DNA
<213> ORGANISM: Homo sapiens

<400> SEQUENCE: 13
cttcgctctg gagcagattt ccaagttgga ggacgagtaa gtcgtgaatt aaattatact    60
cgccagaaga ttggagaaga ggctatgttt aatcctcaac tcatgataca gaccccctaaa   120 gaagaaggtg ctaatgtcct gaccacagaa gcgctcctac aacacctgga ctcggcactc   180
caggccagcc gtgtccatgt atacatgtac aacaggcagt ggaaattgga acatttgtgt   240
tacaaatcag gagagcttat cacagaaaca ggttacatgg atcagataat agaatatctt   300
tacccttgtt tgattattac accctttggac tgcttctggg aaggggcgaa attacagtct   360
gggacagcat acctcctagg taaacctcct ttgcggtgga caaacttcga cccttttggaa   420

```
ttcctggaag agttaaagaa aataaactat caagtggaca gctgggagga aatgctgaat      480
aaggctgagg ttggtcatgg ttacatggac cgcccctgcc tcaatccggc cgatccagac      540
tgccccgcca cagcccccaa caaaaattca accaaacctc ttgatatggc ccttgttttg      600
aatggtggat gtcatggctt atccagaaag tatatgcact ggcaggagga gttgattgtg      660
ggtggcacag tcaagaacag cactggaaaa ctcgtcagcg cccatgccct gcagaccatg      720
ttccagttaa tgactcccaa gcaaatgtac gagcacttc                             759
```

<210> SEQ ID NO 14
<211> LENGTH: 557
<212> TYPE: DNA
<213> ORGANISM: Homo sapiens

<400> SEQUENCE: 14

```
cttcgctctg gagcagattt ccaaggggaa ggctactggc cggaaagcgc cgctgtggct      60
gagagcgaag tttcagagac tcttatttaa actgggttgt tacattcaaa aaaactgcgg      120
caagttcttg gttgtgggcc tcctcatatt tggggccttc gcggtgggat taaaagcagc      180
gaacctcgag accaacgtgg aggagctgtg gtggaagtt ggaggacgag taagtcgtga       240
attaaattat actcgccaga agattggaga agaggctatg tttaatcctc aactcatgat      300
acagacccct aaagaagaag gtgctaatgt cctgaccaca gaagcgctcc tacaacacct      360
ggactcggca ctccaggcca gccgtgtcca tgtatacatg tacaacaggc agtggaaatt      420
ggaacatttg tgttacaaat caggaggagt tgattgtggg tggcacagtc aagaacagca      480
ctggaaaact cgtcagcgcc catgccctgc agaccatgtt ccagttaatg actcccaagc      540
aaatgtacga gcacttc                                                     557
```

<210> SEQ ID NO 15
<211> LENGTH: 394
<212> TYPE: DNA
<213> ORGANISM: Homo sapiens

<400> SEQUENCE: 15

```
cttcgctctg gagcagattt ccaaggggaa ggctactggc cggaaagcgc cgctgtggct      60
gagagcgaag tttcagagac tcttatttaa actgggttgt tacattcaaa aaaactgcgg      120
caagttcttg gttgtgggcc tcctcatatt tggggccttc gcggtgggat taaaagcagc      180
gaacctcgag accaacaaaa attcaaccaa acctcttgat atggcccttg ttttgaatgg      240
tggatgtcat ggcttatcca gaaagtatat gcactggcag gaggagttga ttgtgggtgg      300
cacagtcaag aacagcactg gaaaactcgt cagcgcccat gccctgcaga ccatgttcca      360
gttaatgact cccaagcaaa tgtacgagca cttc                                  394
```

<210> SEQ ID NO 16
<211> LENGTH: 239
<212> TYPE: DNA
<213> ORGANISM: Homo sapiens

<400> SEQUENCE: 16

```
cttcgctctg gagcagattt ccaaggggaa ggctactggc cggaaagcgc cgctgtggct      60
gagagcgaag tttcagagac tcttatttaa actgggttgt tacattcaaa aaaactgcgg      120
caagttcttg gttgattgtg ggtggcacag tcaagaacag cactggaaaa ctcgtcagcg      180
cccatgccct gcagaccatg ttccagttaa tgactcccaa gcaaatgtac gagcacttc      239
```

```
<210> SEQ ID NO 17
<211> LENGTH: 21
<212> TYPE: DNA
<213> ORGANISM: Homo sapiens

<400> SEQUENCE: 17
acactgtgcc catctacgag g                                              21

<210> SEQ ID NO 18
<211> LENGTH: 21
<212> TYPE: DNA
<213> ORGANISM: Homo sapiens

<400> SEQUENCE: 18
aggggccgga ctcgtcatac t                                              21
```